United States Patent [19]

Li et al.

[11] 4,217,493

[45] Aug. 12, 1980

[54] HEMISPHERICAL LAUE CAMERA

[75] Inventors: James C. M. Li, Pittsford; Sungnee G. Chu, Rochester, both of N.Y.

[73] Assignee: The United States of America as represented by the United States Department of Energy, Washington, D.C.

[21] Appl. No.: 45,543

[22] Filed: Jun. 4, 1979

[51] Int. Cl.² ............................................. G01N 23/20
[52] U.S. Cl. .................................... 250/272; 250/273; 250/275
[58] Field of Search ................ 250/272, 273, 274, 275

[56] References Cited

U.S. PATENT DOCUMENTS 3,764,809   10/1973   Haas ..................................... 250/275

OTHER PUBLICATIONS

"New Conical Camera for Single Crystal Orientation by Means of X-Rays", Arguello, Review of Scientific Instruments, vol. 38, No. 5, May, 1967, pp. 598–600.

*Primary Examiner*—Craig E. Church
*Attorney, Agent, or Firm*—R. V. Lupo; Leonard Belkin; Cornell D. Cornish

[57] ABSTRACT

A hemispherical Laue camera comprises a crystal sample mount for positioning a sample to be analyzed at the center of sphere of a hemispherical, X-radiation sensitive film cassette, a collimator, a stationary or rotating sample mount and a set of standard spherical projection spheres. X-radiation generated from an external source is directed through the collimator to impinge onto the single crystal sample on the stationary mount. The diffracted beam is recorded on the hemispherical X-radiation sensitive film mounted inside the hemispherical film cassette in either transmission or back-reflection geometry. The distances travelled by X-radiation diffracted from the crystal to the hemispherical film are the same for all crystal planes which satisfy Bragg's Law. The recorded diffraction spots or Laue spots on the film thereby preserve both the symmetry information of the crystal structure and the relative intensities which are directly related to the relative structure factors of the crystal orientations. The diffraction pattern on the exposed film is compared with the known diffraction pattern on one of the standard spherical projection spheres for a specific crystal structure to determine the orientation of the crystal sample. By replacing the stationary sample support with a rotating sample mount, the hemispherical Laue camera can be used for crystal structure determination in a manner previously provided in conventional Debye-Scherrer cameras.

13 Claims, 6 Drawing Figures

U.S. Patent  Aug. 12, 1980  Sheet 1 of 2  4,217,493
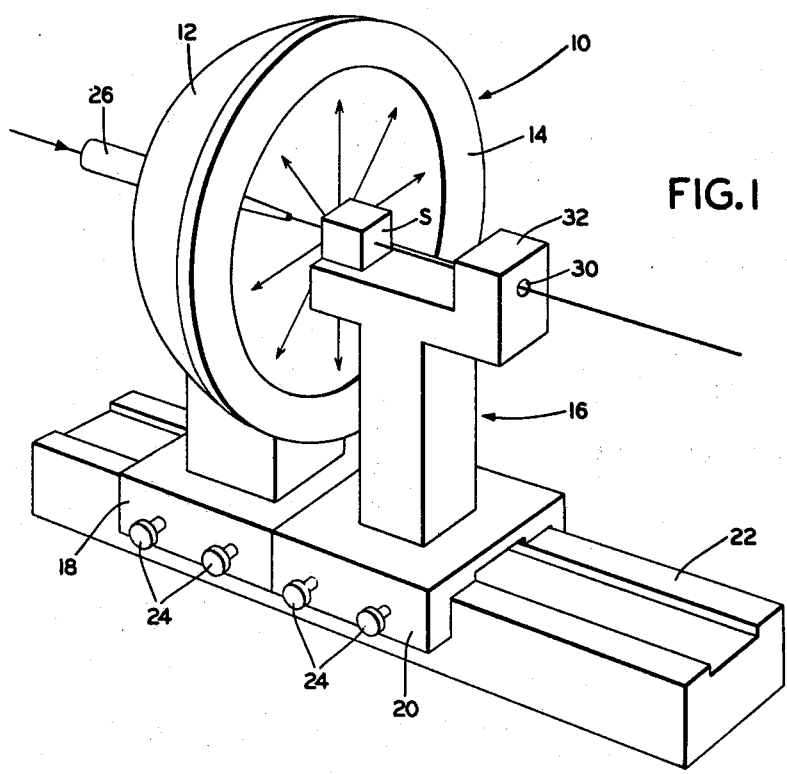
FIG. 1
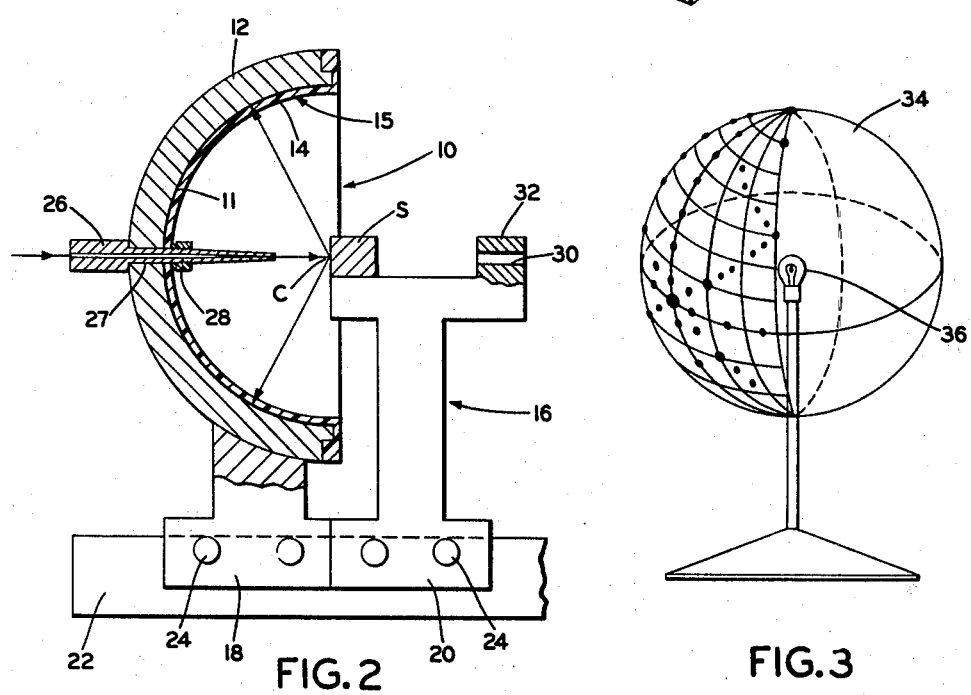
FIG. 2
FIG. 3

HEMISPHERICAL LAUE CAMERA

ORIGIN OF THE INVENTION

The invention described herein is made in the course of, or under contract with, the United States Department of Energy.

TECHNICAL FIELD

The present invention is directed generally toward crystallography cameras, and more particularly, toward a novel Laue camera having a hemispherical film cassette carrying hemispherical, X-radiation sensitive film for eliminating diffraction pattern distortion.

BACKGROUND ART

Crystalline materials exhibit an ordered and repeated structure throughout the extent of the crystal. If a set of reference axes is defined at any point within the crystal, the atoms within the structure may be considered to lie in planes which intercept the reference axes at various distances. The number and types of planes which a crystal possesses, the spacing between the planes and the angles which these planes make with the reference axes are important characteristics of the particular crystal under study.

Crystal orientation is generally determined by X-ray diffraction techniques. Laue in 1913 postulated that the atoms in a crystal structure might serve as a three-dimensional diffraction grating for X-rays because experimentation had correctly indicated that X-ray wavelengths are on the order of $10^{-8}$ cm which is about the same as the interatomic spacing in the solid.

In practice, the surface of a crystal sample is irradiated by a collimated beam of X-radiation, and a flat, X-radiation sensitive film is exposed to the diffracted radiation to develop a diffraction pattern or "Laue photograph". The diffracted beams which form the diffraction pattern satisfy Bragg's Law, $n\lambda = 2d \sin \theta$, where n is the order of refraction, $\lambda$ is the wavelength of the radiation in Angstrom units, d is the crystalline interplanar spacing in Angstrom units, and $\theta$ is the angle between the radiation and the normal of the crystalline planes. The resultant photograph is used to provide the information of crystal orientation.

In practice, however, analysis of the Laue photograph cannot be made directly from the diffraction pattern developed from the exposed film because the pattern is distorted as a result of gnomonic projection of diffraction spots on a unit sphere from a point (crystal) to a flat film along unequal paths. In order to compensate for this distortion, the angles obtained from the diffraction pattern spots on the photograph must be transformed onto a Wulff net by using a Greninger chart for standard stereographic projection examination.

The orientation of each spot is determined by trial and error by first assigning an orientation to one of the bright spots and trying to match the angles between the neighboring spots from the tabulated interplanar angles for the specific crystal structure. Bearing in mind that a typical Laue photograph may comprise 50 or more spots, the work is tedious and time consuming. The method becomes extremely difficult for indexing high index orientations as well as any orientation for structures of low symmetry. An alternative method is to reorient the crystal to the orientation of one of the bright spots from the first photograph and take another Laue photograph. The above procedure can then be repeated.

In view of all these disadvantages of the conventional Laue photography, a primary object of the present invention is to provide a new and improved Laue camera for direct crystal orientation determination with undistorted Laue photographs thereby eliminating the need for the Greninger chart, the stereographic projection and the work of matching interplanar angles.

Another object is to provide a new and improved Laue camera that is easier and faster to operate for a person with no previous experience in crystal orientation determination.

DISCLOSURE OF INVENTION

A Laue camera, in accordance with the invention, comprises a crystal sample mount for locating a sample to be analyzed at the center of sphere of a hemispherical, X-ray sensitive film cassette. An X-ray collimator directs a beam of X-radiation generated by an external source to impinge on the crystal sample. The hemispherical film is exposed to X-radiation diffracted from the sample to provide a Laue photograph.

In one embodiment, the collimated, X-radiation beam is directed through a hole formed in the hemispherical film cassette where the collimator is attached to impinge on the surface of the crystal sample facing the film to expose the film to the diffraction pattern of the X-ray generated by back reflection from the crystal. In another embodiment, the collimated beam of radiation is directed to impinge onto the crystal sample opposite the film cassette to expose the film to the diffracted X-radiation beam passing through the body of the crystal. In either embodiment, the crystal holder is stationary and may be a three-angle goniometer to orient the crystal for cutting and slicing while contemporaneously taking a confirming Laue photograph.

The hemispherical shape of the film eliminates distortion of the projected diffraction image because the distances between the crystal sample and every point on the surface of the film are the same, viz, the radius of the hemisphere. After the film is developed, indexing of the diffraction spot is made by matching the photograph with a standard projection sphere provided for various crystal structures.

Because there are equal projection distances for every ray emanating from the crystal to the film, the intensities of the Laue spots are related directly to the relative intensities of the diffracted X-radiation and are not a function of position of the spots on the film, so that the intensity information can be used to calculate crystal structure.

Standard projection transparent spheres with internal light sources are marked with meridian and latitude circles and many low index spots. The relative darkness of the spots is simulated from an actual diffraction pattern for a certain X-ray source. Each sphere corresponds to a certain crystal structure.

One important advantage of this invention, besides providing distortion-free Laue photographs, is that the function of the hemispherical Laue camera can be converted from crystal orientation determination directly into crystal structure determination by replacing a stationary crystal sample mount with a rotating crystal sample mount. The rotation of the crystal along the vertical axis through the center of sphere of the hemispherical camera converts the Laue spots into parallel arcs. The angles between the arcs can be used for determination of the lattice spacing between the corresponding diffraction planes. The hemispherical, Laue camera of the invention in this mode resembles the conventional Debye-Scherrer camera except that the latter uses a cylindrical film cassette.

Another advantage is that, as stated above, the recorded Laue spots on the hemispherical film preserve the relative intensities of the X-ray beam diffracted from the crystal planes of different orientations. Since the intensity of the X-ray beam diffracted from certain crystal plane is proportional to the square of the structure factor associated with the orientation of that plane, the relative intensitites of the Laue spots provide direct information of the structure factors associated with different orientations of the crystal planes.

Another object of the present invention, therefore, is to provide a new and improved Laue camera that is convertible between orientation and structure determination modes of operation.

An additional object of the invention is to provide a new and improved Laue camera that preserves the relative intensities of the Laue spots to provide direct structure factor information.

Still other objects and advantages of the present invention will become readily apparent to those skilled in this art from the following detailed description, wherein we have shown and described only the preferred embodiments of the invention, simply by way of illustration of the best modes contemplated by us of carrying out our invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

FIG. 1 is a perspective view of a hemispherical Laue camera having a reflection Laue geometry constructed in accordance with one preferred embodiment of the invention.

FIG. 2 is a cross sectional side view of the embodiment of FIG. 1 having a diffraction pattern recorded with X-radiation reflected from the surface of the crystal and impinging on hemispherical, X-radiation sensitive film;

FIG. 3 is a perspective view of a transparent standard projection sphere having a typical crystal diffraction pattern and meridian and latitude circles printed thereon with a light fixture mounted inside the sphere;

BEST MODE FOR CARRYING OUT THE INVENTION

Figure 4:
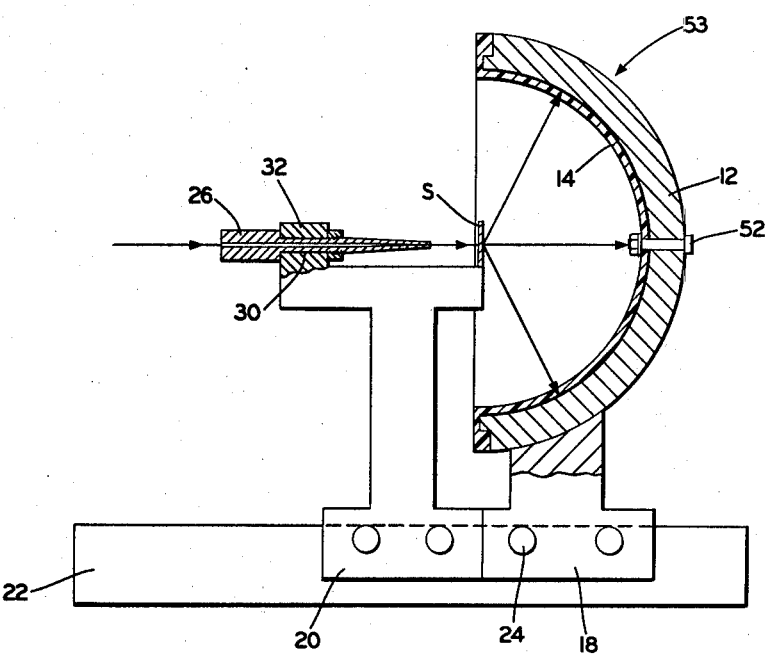
FIG. 4 is a cross sectional side view of a hemispherical Laue camera having a transmission Laue geometry constructed in accordance with a second embodiment of the invention.

Referring to FIGS. 1 and 2, a first embodiment of a novel hemispherical Laue camera 10 in a reflection Laue geometry, in accordance with the invention, comprises a hemispherical, film-carrying cassette 12 having an inner surface 11 for receiving and holding a hemispherical, X-radiation sensitive film 14, and a hemispherical, X-radiation transparent cover 15 for protecting the X-ray film from exposure to light. The center of sphere C of the cassette 12 as well as of the film 14 is coincident with the reflecting surface of a single crystal sample S to be analyzed.

The sample S is positioned on a stationary crystal sample support 16 which may optionally be provided as a conventional, three angle goniometer (not shown) of a type disclosed in U.S. Pat. No. 3,504,178. The cassette 12 and support 16 are located on brackets 18 and 20 that ride on the rail 22 of an X-ray machine of conventional construction with each bracket having thumb screws 24 that extend into contact with the surface of rail 22. The position of the crystal sample S relative to the X-radiation sensitive film 14 can be adjusted by loosening thumb screws 24 and manually moving the bracket 20 on rail 22 until the reflecting surface of crystal S is positioned at the center of sphere C of the film. The position of the bracket 20 is then fixed by tightening bracket 20 onto rail 22 by thumb screws 24.

As best shown in FIG. 2, a collimator 26 is oriented horizontally and located through opening 27 in the shell of cassette 12 and also through the X-radiation sensitive film 14 and film cover 15. The collimator 26 is retained to the cassette 12 by a nut 28 that also secures the film 14 and film cover 15 to the inner surface of cassette 12. The collimator 26, which is of a conventional construction, is positioned on the cassette 12 so as to direct a beam of X-radiation through the center of rotation C of the cassette 12 and film 14.

An external source of X-radiation beam (not shown) generated by the X-ray machine is directed through collimator 26 onto crystal sample S. A diffraction pattern formed by X-radiation reflected from the surface of the crystal sample S impinges on the inner surface of X-radiation sensitive film 14 through the film cover 15, as shown by the arrows. Any X-radiation transmitted through the body of the sample S passes through aperture 30 formed in upwardly extending portion 32 of support 16. Although not shown in FIG. 2, the same beam stopper 52 (FIG. 4) used in the transmission Laue geometry, described below, may be located in aperture 30 to function as a stop for the X-radiation beam. The upwardly extending portion 32 of the support 15 forms the collimator support in the Laue camera in accordance with a second preferred embodiment of the invention to be described below in connection with FIG. 4.

Still referring to FIG. 2, it is apparent that the distances between the reflecting point C of crystal sample S and all points on the inner surface of hemispherical film 14 are equal so that there is no distortion of the diffraction pattern caused by unequal path lengths as in conventional Laue photography wherein the diffracion rays emanate from a point source to a planar film surface. As a result of distortion-free diffraction pattern formed on the hemispherical film 14 when exposed to the reflected X-radiation, there is no need for conventional analysis using the Greninger chart or other means. Furthermore, the solid angle subtended at the crystal sample S by the hemispherical film 14 is $2\pi$ which is more than twice the conventional angle subtended by planar film.

In use, after the position of crystal sample S is adjusted to the center of sphere C of hemispherical film 14 in the cassette 12, the surface of the sample is irradiated by a collimated beam of X-radiation through collimator 26 from the external source (not shown). Following exposure of the film 14 to the reflected X-radiation, the film is developed and the photograph compared to a standard projection sphere 34 (FIG. 3) by rotating the hemispherical film on the surface of the standard projection sphere to match the pattern of the Laue spots on the film to that on the standard sphere.

The standard projection sphere 34 is a transparent sphere having imprinted thereon spot patterns denoting particular crystallographic orientations for a certain crystal structure as well as reference meridian and lattice circles, as shown in FIG. 3. The standard 34 is internally illuminated by a conventional lamp 36, as shown, to emphasize the locations of the spots within the diffraction pattern and reference circles. The Laue spots constituting the diffraction patterns and reference circles on the developed film enable the observer to determine crystallographic orientation of the sample by comparison of the Laue photographs with standards in a known manner.

Referring to FIG. 4, a hemispherical Laue camera 53 in a transmission Laue geometry in accordance with a second embodiment of the invention is shown, wherein the collimator 26 is mounted in the aperture 30 to upstanding portion 32 of the crystal support 16. Aperture 27 within the film cassette 12 is enclosed by a bolt or beam stopper 52 which maintains film 14 within the cassette and also serves as a stop for the direct beam of X-radiaton passing through crystal sample S in a manner described above with respect to FIGS. 1 and 2.

In accordance with the embodiment of FIG. 4, the sample S is positioned at the center of sphere C of the hemispherical film 14 and is irradiated by a collimated beam of X-radiation from an external source (not shown) positioned at a side of the sample S opposite the film 14. Diffraction of the beam of X-radiation passing through the body of the sample S is impinged on the surface of the film 14 through the X-radiation transparent cover 15 to be developed into a transmission type, Laue photograph.

Figure 5:
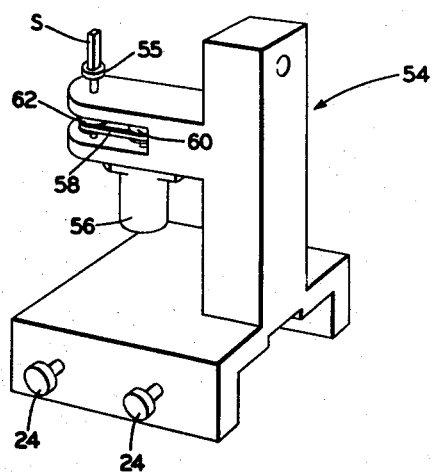
FIG. 5 is a perspective view of a motor operated, spinning table for rotating the crystal sample to generate intensity modulated diffraction bands onto the hemispherical film for crystallographic structure computations.
Figure 6:
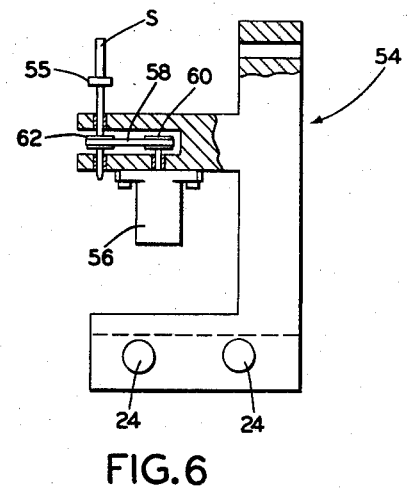
FIG. 6 is a cross sectional side view of the spinning table shown in FIG. 5.

Referring now to FIGS. 5 and 6, an alternate crystal holder 54, adapted to be mounted on rail 22 in place of the mount 15 shown in FIGS. 1, 2 and 4, has a sample table 55 that is rotated by an electric motor 56 through a drive band 58 extending between a spindle 60 on the motor shaft and another spindle 62 on the shaft of the table 55. When energized, the motor 56 spins a crystal sample S on table 55 to generate parallel diffraction bands rather than spots on the surface of hemispherical film 14. The bands or rings caused by diffraction of X-radiation in either the transmission or reflection mode by the rotating crystal sample S have relative intensities that are functions of the structure factors of crystallographic structure.

The spacings between the bands measured in angles can be used to calculate lattice spacings between the diffraction planes, which thereby determine the lattice parameter. Along with the symmetry of the Laue photograph and the structure factors from the relative intensities, the crystal structure can be determined.

In view of the foregoing, it can be appreciated that the provision of the hemispherical film 14 in a Laue camera significantly improves the utility of the instrument because resultant Laue photographs are distortion-free, eliminating the requirement of geometrical transformation of the spot angles prior to analysis which has become standard laboratory practice. Furthermore, the construction of the camera, in accordance with the invention, enables utilization alternatively in reflection or transmission mode Laue photography, as is apparent from a comparison of FIGS. 2 and 4 and from the disclosure. The preservation of spot intensity information further enables direct computation of structure factors of the sample.

In this disclosure, there is shown and described only the preferred embodiments of the invention, but, as aforementioned, it is to be understood that the invention is capable of use in various other combinations and environments and is capable of changes or modifications within the scope of the inventive concept as expressed herein. For example, it is not necessary for the film cassette 12 itself to be hemispherical as long as the film 14 is hemispherical either by its own construction or by support structures. The hemispherical shape of the cassette 12 is preferred, however, since the inner surface of the cassette in contact with film 14 will tend to eliminate any geometrical distortions in the film itself due to buckling or warping.

We claim:

1. A crystallography camera, comprising means for holding a hemispherical, X-radiation sensitive film, a mount for supporting a crystal sample at the spherical center of said film and means for directing a beam of X-radiation generated by an external source for impingement onto a surface of the crystal sample, said hemispherical film being exposed to X-radiation diffracted by said crystal sample.

2. The camera of claim 1, wherein said film holding means comprises a hemispherical body having its spherical center substantially coincident to the crystal sample.

3. The camera of claim 2, wherein said beam collimating means extends through the center of the surface of said hemispherical body to cause a collimated beam to impinge on a surface of said crystal sample facing said body, said film being exposed to a diffraction pattern caused by reflection of X-radiation from said facing surface of said sample.

4. The camera of claim 2, wherein said beam collimating means is positioned on a side of the sample opposite said hemispherical body, said film being exposed to a diffraction pattern caused by transmission of X-radiation through said sample.

5. The camera of claim 1, including means for adjusting a position of said sample support relative to said X-radiation sensitive film.

6. The camera of claim 1, wherein said crystal sample mount includes means for rotating said crystal.

7. The camera of claim 6, wherein said sample rotating means includes an electric motor.

8. The camera of claim 1, including a hemispherical, X-radiation sensitive film mounted to said film holding means for exposure to X-radiation diffracted by said crystal sample.

9. A method of obtaining a distortionless photograph, comprising the steps of positioning a crystal sample at the center of rotation of a hemispherical, X-radiation sensitive film, irradiating a surface of said sample with a beam of X-radiation, exposing said film to X-radiation diffracted by said sample and developing said exposed film.

10. The method of claim 9, wherein said irradiating step includes directing the beam onto a surface of said sample facing said film and said exposing step includes exposing said film to X-radiation reflected from said facing surface of said sample.

11. The method of claim 9, wherein said irradiating step includes directing the beam onto a surface of said sample opposite said film and said exposing step includes exposing the film to X-radiation passing through said sample.

12. In combination:
a crystallography camera, comprising means for holding a hemispherical, X-radiation sensitive film, a mount for supporting a crystal sample at the spherical center of said film and means for directing a beam of X-radiation generated by an external source for impingement onto a surface of the crystal sample, said hemispherical film being exposed to X-radiation diffracted by said crystal sample; and
standard projection transparent sphere means for crystal structures, said sphere means having imprinted thereon projection spots for various crystal lattice structures and meridian and latitude circles to be compared with corresponding photographs obtained by said camera.

13. The combination of claim 12, including illuminating lamp means inside said standard sphere means.

* * * * *